United States Patent
Jerebko

(10) Patent No.: US 9,129,362 B2
(45) Date of Patent: Sep. 8, 2015

(54) SEMANTIC NAVIGATION AND LESION MAPPING FROM DIGITAL BREAST TOMOSYNTHESIS

(71) Applicant: SIEMENS AKTIENGESELLSCHAFT, Munich (DE)

(72) Inventor: Anna Jerebko, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 191 days.

(21) Appl. No.: 13/899,988

(22) Filed: May 22, 2013

(65) Prior Publication Data

US 2014/0348404 A1     Nov. 27, 2014

(51) Int. Cl.
    *G06T 7/00*           (2006.01)
    *A61B 6/00*         (2006.01)

(52) U.S. Cl.
    CPC ............... *G06T 7/0012* (2013.01); *A61B 6/502* (2013.01); *A61B 6/5217* (2013.01); *G06T 2207/10112* (2013.01); *G06T 2207/30068* (2013.01)

(58) Field of Classification Search
    CPC .................. G06T 7/0012; G06T 2207/10112; G06T 2207/30068; A61B 6/502; A61B 6/5217
    See application file for complete search history.

(56) References Cited

U.S. PATENT DOCUMENTS 5,757,880 A *   5/1998   Colomb ........................ 378/37
2012/0157819 A1 *   6/2012   Jerebko et al. ................ 600/407

OTHER PUBLICATIONS van Schie et al., "Mass detection in reconstructed digital breast tomosynthesis volumes with a computer-aided detection system trained on 2D mammograms", Apr. 2013, Medical Physics 40, 041902-1-041902-11.*
van Schie et al., "Estimating corresponding locations in ipsilateral breast tomosynthesis views", Medical Imaging 2011: Computer-Aided Diagnosis, Proc. of SPIE vol. 7963, 796306-1-796306-7.*
Wels et al., "Data-Driven Breast Decompression and Lesion Mapping from Digital Breast Tomosynthesis", MICCAI 2012, Part I, LNCS 7510, pp. 438-446.*
Tanner et al, "Large breast compressions: Observations and evaluation of simulations", Med. Phys. 38 (2), Feb. 2011, pp. 682-690.
Van Schie et al, "Correlating locations in ipsilateral breast tomosynthesis views using an analytical hemispherical compression model", IOP Publishing, Phys. Med. Biol. 56 (Jul. 2011), pp. 4715-4730.
Samani et al., "Biomechanical 3-D Finite Element Modeling of the Human Breast Using MRI Data", IEEE Transactions on Medical Imaging, vol. 20, No. 4, Apr. 2001,pp. 271-279.

* cited by examiner

*Primary Examiner* — Katrina Fujita
(74) *Attorney, Agent, or Firm* — Laurence A. Greenberg; Werner H. Stemer; Ralph E. Locher

(57) ABSTRACT

A method, a system, a computer program and a computer program product, as well as a computer-readable storage medium, enables navigating between different medical images and localizing dedicated positions in the images. The medical images may be digital breast tomosynthesis (DBT) images, full-field digital mammography system (FFDM) images and magnetic resonance (MR) images. The process is based on a shape prediction algorithm and a computer-aided detection/diagnosis (CAD) algorithm in order to find a corresponding second position in the at least one second image.

20 Claims, 3 Drawing Sheets

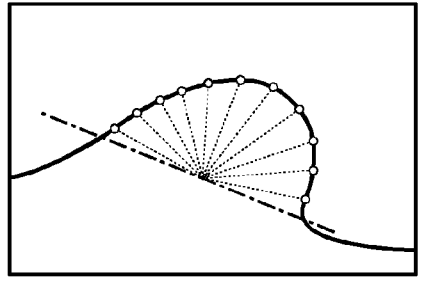
FIG 4
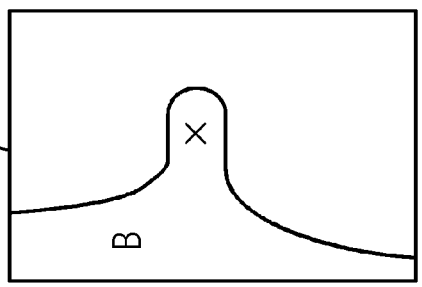
FIG 5
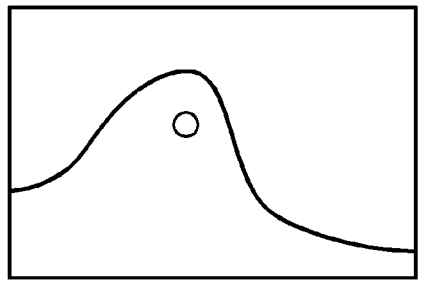
FIG 6
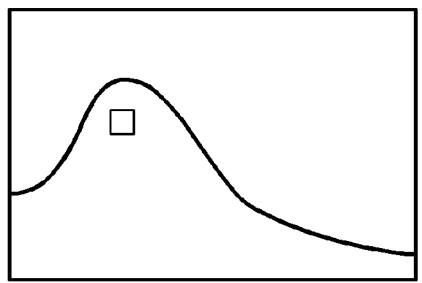
FIG 7
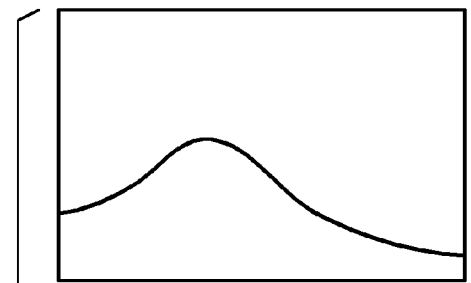
FIG 8 · · ·

SEMANTIC NAVIGATION AND LESION MAPPING FROM DIGITAL BREAST TOMOSYNTHESIS

BACKGROUND OF THE INVENTION

Field of the Invention

The present invention generally refers to medical imaging and image processing and, more particularly, to semantic navigation and lesion mapping in different scans or different images, acquired by digital breast tomosynthesis (DBT) or mammography.

Numerous clinical studies show that mammography helps to achieve a reduction in breast cancer mortality rate by 30% to 50%. Early detection is assumed to significantly improve outcomes. Computed tomography (CT) and magnetic resonance imaging (MRI) are currently the most effective breast cancer screening techniques. Conventional mammography techniques rely on a pair of two-dimensional X-ray images of the female breast, taken from two different directions with the breast being compressed in different ways. The breast tissue to be examined is compressed and held between two compression plates to ensure that the entire breast tissue is viewed. Nowadays, full-field digital mammography systems (FFDM) are commonly used.

Recently, digital breast tomosynthesis (DBT) is increasingly replacing common 2D mammography for differential diagnoses and is in discussion for screening. DBT images provide more information than regular FFDM images for early detection of anomalies and cancer.

DBT provides 3D image volumes of the compressed breast that are reconstructed from multiple 2D projections acquired at varying angles. Being a 3D imaging modality DBT naturally allows superior spatial localization of suspicious lesions. A mediolateral-oblique (MLO) and, typically, a second cranio-caudal (CC) scan is acquired during an examination. The breast is compressed differently for MLO and CC scans. For reporting and surgical planning it is common clinical practice to mark the lesions in the scans and to communicate the rough localization of suspicious findings in the uncompressed breast via schematic 2D drawings. The latter naturally suffers from inaccuracies and can often only be dissolved by additional, potentially ionizing and costly, imaging. Providing more accurate lesion localization in the uncompressed breast, e.g., in terms of a 3D rendering view, without additional imaging has the potential not only to facilitate surgical planning and related procedures, e.g., placing pre-operative markers but also to resolve the problem of ambiguous mapping of multiple similarly looking lesions between CC, MLO DBT and FFDM scans including previously acquired images.

For precise navigation and comparison with follow-up images or images acquired in the previous years (so called priors, or prior images of the same patient) highly non-rigid registration methods, based on internal breast structures are required. A major drawback of systems using image registration to be seen in that they are very time consuming. Further, they are not suitable for real time implementation, especially on viewing workstations without a powerful graphic card.

In order to overcome the above-mentioned disadvantages in performance, on-line navigation systems based on a simple geometrical decompressed breast model are therefore used [cf: paper Van Schie, G., Tanner, C., Snoeren, P., Samulski, M., Leifland, K., Wallis, M. G., Karssemeijer, N.: "Correlating Locations in Ipsilateral Breast Tomosynthesis Views Using an Analytical Hemispherical Compression Model", Phys. Med. Biol. 56(15), 4715-4730 (2011)]. However, these systems are not sufficiently precise because they do not take into account the internal breast structures. The breast is placed and rolled more or less differently every time it is compressed and therefore internal tissue is displaced even in the same position MLO or CC. Therefore it is not possible to precisely navigate between the two scans without matching the internal tissue structures. Generally, it is a major issue to improve quality and precision of mapping techniques. Interpreting a mammogram is difficult due to breast tissue overlapping and superimpositions, which make small cancerous tissue regions and other pathological tissue anomalies sometimes undetectable. In this case precise mapping between two or more scans of the same breast can increase doctor confidence and sensitivity and help to eliminate false positive detections.

It is often necessary to compare and review different scans of the breast for diagnostic and/or surgical planning. Thus, the scans may refer to different compression states of the breast. A first scan typically refers to a compressed state of the breast (particularly during imaging) and a second image (which also might be a model) may refer to a differently compressed breast. In practice it is essential to mark the lesions in both scans and, preferably, localize suspicious findings also in the uncompressed breast model.

In order to be able to compare different images of the breast in different compression states a huge body of literature deals with biomechanical breast modeling (see, for example, Tanner, C., White, M., Guarino, S., Hall-Craggs, M. A., Douek, M., Hawkes, D. J.: "Large Breast Compressions: Observations and Evaluation of Simulations", Med. Phys. 38(2), 682-690 (2011) 3 and Samani, A., Bishop, J., Yaffe, M. J., Plewes, D. B.: "Biomechanical 3-D Finite Element Modeling of the Human Breast Using MRI Data", IEEE Trans. Med. Imag. 20(4), 271-279 (2001)).

Van Schie et al. also deals with correlating locations in digital breast tomosynthesis (van Schie, G., Tanner, C., Snoeren, P., Samulski, M., Leifland, K., Wallis, M. G., Karssemeijer, N.: "Correlating Locations in Ipsilateral Breast Tomosynthesis Views Using an Analytical Hemispherical Compression Model", Phys. Med. Biol. 56(15), 4715-4730 (2011)). However, in this approach the behavior of the breasts during compression/decompression is explicitly modeled by approximating breast tissue properties. Regions are mapped by intermediately mapping then to a decompressed version of the initial geometric model that has been matched to the compressed breast before. The matching region in the ipsilateral view is finally found after rotation and repeated compression. Thus, a drawback of this approach is that it is necessary to explicitly model tissue behavior.

BRIEF SUMMARY OF THE INVENTION

It is accordingly an object of the invention to provide a method for navigating between different medical images and for localizing dedicated positions in different medical images, which is suitable for a real time implementation. Further, this method should be usable on a (normal) workstation without enhanced processing capabilities. Thus, it should be possible to use the method with a normal graphic card (without specific requirements for graphical processing). Further, it should be possible to predict the shape of the uncompressed breast directly and without intermediate steps (for example repeated compression/decompression steps) and without explicitly modeling tissue behavior. Moreover, the method for localizing dedicated positions in different breast scans and for navigating between the different scans should only rely on data and should not involve any explicit biomechanical modeling of deformations, e.g. induced by gravity or compression.

Finally, accuracy and precision of navigation and localization procedures should be improved.

With the foregoing and other objects in view there is provided, in accordance with the invention, a localization and navigation tool for navigating between different medical images and for localizing dedicated positions in the images, particularly in digital breast tomosynthesis images of the breast in different compression states. The imaging method may be performed on a device with an X-ray emitting source, an X-ray detector and a computer node for image and data processing of the acquired images, which may be coupled over a network. The novel method comprises the following steps:

providing an input interface for acquiring a first image and at least one second image from a breast. According to a preferred embodiment of present invention the first image refers to a breast image in a first compression state (e.g. compressed) and the second image refers to an image from the breast in a second compression state (e.g. differently compressed);

receiving a user input signal on a user interface for marking a first position in the first image;

applying a shape prediction algorithm in order to find a rough estimation for a corresponding second position in at least one second image (the position mapping may also be applied to several—second—images); the shape prediction algorithm may also be used in order to predict the decompressed shape for the first and second image and to obtain a coordinate transformation that maps the user-marked first position in the first image into a corresponding second position in at least one second image;

applying a CAD algorithm to both breast images to detect anatomical structures of multiple classes;

refining the rough coordinate transformation for mapping the locations in the 1st image into corresponding second positions in the at least one 2nd image by means of processing and matching landmarks of corresponding classes (e.g. by means of random sample consensus algorithm);

localizing the second position in the second image based on the refined rough coordinate transformation, wherein the method is executed without explicitly registering the images, but only applying the refined coordinate transformation to the provided location in the first image.

With the above and other objects in view there is also provided, in accordance with the invention, a computer system for navigating between different medical images and for localizing dedicated positions in said images, particularly in digital breast tomosynthesis images of the breast in different compression states. The imaging method may be performed on a device with an X-ray emitting source, an X-ray detector and a computer node for image and data processing of the acquired images, which may be coupled over a network. The novel system comprises:

An input interface for acquiring a first image in a first compression state and at least one second image from a breast in another compression state.

An input signal generation unit for receiving a user input signal on a user interface for marking a first position in the first image.

A shape prediction module which is adapted to apply a shape prediction algorithm in order to predict the decompressed shape for the first and second image and to obtain a rough coordinate transformation that maps the user-marked first position in the first image into a corresponding second position in at least one second image.

A CAD module, which might be implemented in common with the shape prediction module and which is adapted to apply a CAD algorithm to both breast images to detect anatomical structures of multiple classes.

A mapper for refining the rough coordinate transformation for mapping the locations in the 1st image into corresponding second positions in the at least one 2nd image by means of processing and matching landmarks of corresponding classes (e.g. by means of random sample consensus algorithm).

A localizer for localizing the second position in the second image based on the refined rough coordinate transformation, wherein the method is executed without explicitly registering the images, but only applying the refined coordinate transformation to the provided location in the first image.

According to an aspect of present invention the shape prediction algorithm is based on a geometrical statistical breast model, which is constructed based purely on a set of training data.

According to a further aspect of present invention the statistical breast model is based on a set of shape parameters.

According to an aspect of present invention the method and/or the shape prediction algorithm is/are processed on-line and/or in pre-computation.

According to an aspect of present invention the CAD algorithm is applied to the first and to the second image. Preferably, the CAD algorithm is a machine learning-based algorithm which processes multiple classes of anatomical structures.

According to an aspect of present the method for finding the corresponding second position in the second image is based on first estimating a rough coordinate transformation from simple anatomical landmarks like skin, nipple and pectoral muscle based on the decompressed shape model and second, refining the coordinate transformation based on the internal anatomical landmarks provided by a CAD algorithm.

The invention further refers to a computer based system which is adapted for executing the method described above.

The invention also relates to a computer program product which is loaded or may be loaded in a memory of a computer and with computer readable instructions for executing the method according to one of the method claims, mentioned above, if the instructions are executed on the computer.

Finally, the invention relates to a non-transitory computer-readable storage medium with computer readable instructions for executing the method according to the method described above.

Other features which are considered as characteristic for the invention are set forth in the appended claims.

Although the invention is illustrated and described herein as embodied in a semantic navigation and lesion mapping from digital breast tomosynthesis, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIGS. 4-8 depict images of a breast with anatomical entities and contours of a surface re-sampling planes in the MLO plane (FIG. 4) and in different compression states (FIG. 5-8).

DETAILED DESCRIPTION OF THE INVENTION

Figure 1:
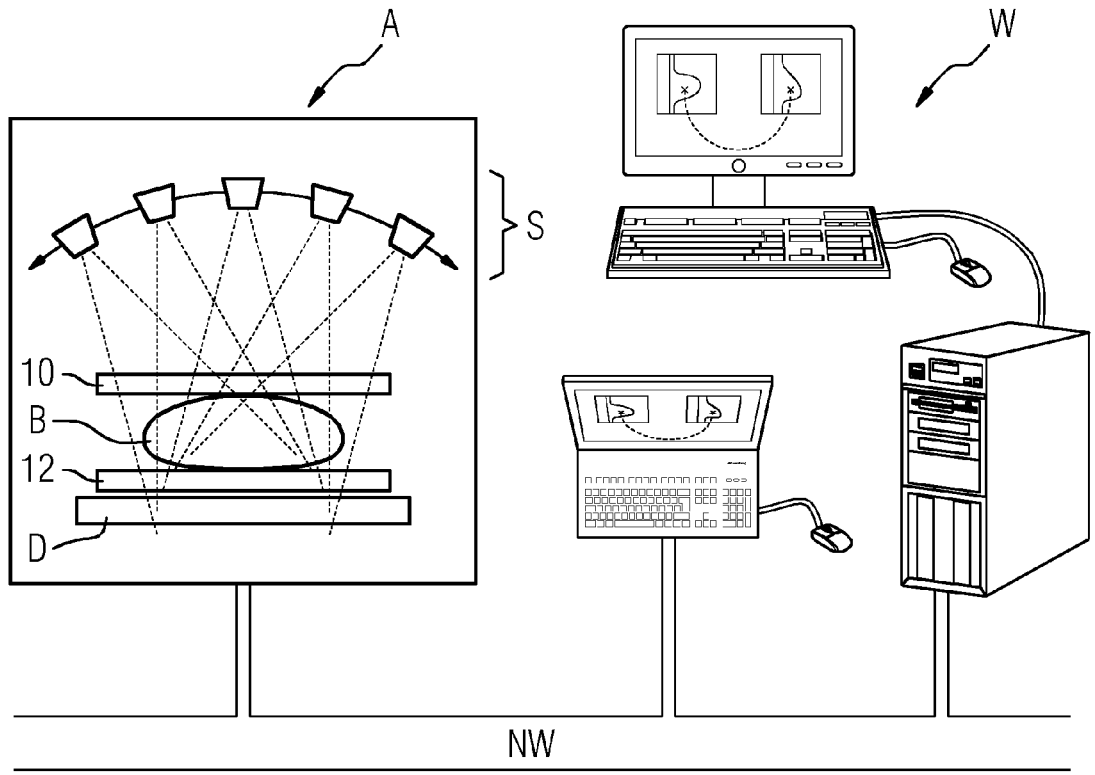
FIG. 1 shows a schematic illustration of a medical imaging system with a computer for navigating between and localizing dedicated positions according to a preferred embodiment of present invention.

Embodiments of the present invention propose solutions for navigating between and localizing dedicated positions in differently compressed breast scans which do not have the disadvantages of the prior art systems.

First, the following provides for a short definition and explanation of a variety of terms that are used in this specification.

The term "navigating" refers to operating and/or controlling different image displays, particularly on a monitor of a medical examination workstation. For a physician it is necessary to navigate through a stack of (volume) scans and to find his way through different images scans for example provided by digital breast tomosynthesis, full field digital mammography or another mammography system. Thus, navigating refers to guiding through different images.

Generally, present invention refers to localizing dedicated positions in these different medical images. "Localizing" refers to find a position of a specific structure in the images. During examination the physician is usually confronted with one or more DBT slices, a simulated mammogram and for example other images, like full field digital mammography images (FFDM). If a region of interest or a specific anatomical structure (lesion) may be found in one of these images (for example in a specific DBT slice), the physician may mark this specific region in the first image and want to localize this position or a corresponding position in all the other images or slices. Localizing thus refers to finding a specific position in three-dimensional or two-dimensional space. Localizing also refers to mapping a first position to a corresponding position in at least one other scan.

Generally, the method is not restricted to specific dedicated positions. Dedicated positions may refer to anatomical regions of interest, to lesions, to clusters of regions of calcifications, to blood vessels and/or to other structures.

The input interface is usually a graphical user interface on which a user is able to input a signal in order to mark a specific position in an image in order to select this position for further processing. This position is then used to find corresponding positions of the same patient in the other scans or images.

Typically, the first compression state refers to a compression state which is used during image acquisition (by means of a compression plate and a detector cover surface, compressing the breast for making visible the anatomical structures). The second compression state, however, refers to a compression state which is different from the first compression state of the breast. It should be noted that the second compression state may also refer to other compression states (for example a compressed state with a lesser degree than the first compression state or compressed under a different angle).

It is also within the scope of protection that the transfer or mapping of the first position in the first image is to be made to another image, which does not necessarily be an image of the breast in another compression state, but might also be any other image, like any other computer generated visualization, which could be a model of the breast, an image of the breast, acquired with another modality, a prior scan of the patient's breast or other image displays.

"Marking" the first position in the first image is usually executed by means of a user signal, inputted on the graphical user interface. Marking, thus, refers to defining a point or an anatomical region in the image.

The shape prediction algorithm is a computer-implemented algorithm, which is executed fully automatically and which serves to find a rough estimation for a corresponding second position in the second image. In other embodiments of present invention it is also possible to apply the method to several further images, so that a first position in a first image is to be mapped or transferred to several corresponding positions in several second images. In this embodiment the number of second images is identical with the number of second positions.

The CAD algorithm refers to a computer aided detection and/or diagnosis algorithm, which is also executed fully automatically. The CAD algorithm is optimized for maximally high sensitivity. The CAD algorithm does not necessarily need to have very high specificity. The CAD algorithm could be trained as a machine learning algorithm in that output data are fed back as input parameters to the algorithm so that the algorithm "learns" to better detect lesions. The CAD algorithm is applied to detect not only medical relevant lesions, such as clusters of micro- and macro-calcification and masses, but also multiple classes of anatomically relevant structures, such as blood vessels and their bifurcations, cooper ligaments, milk ducts, cysts, scars, lymph nodes and other anatomical landmarks. This step could be performed online in the local vicinity of a click point or a user-marked point and in the vicinity of a point mapped to another view (or image scan) in order to reduce the computation time.

The term "landmark" refers to anatomical and/or medical relevant landmarks. These landmarks are visible in the images to be processed.

The term "localizing" refers to outputting a position within an image to be displayed on a monitor, printed in a hardcopy report, stored in a DICOM object such as structured report or DICOM image or a secondary capture image or otherwise stored in a PACS system or any storage device. Generally, localizing refers to marking a position on the image directly (for example as an overlay structure, like a cross line or a circle or ellipse shaped form, surrounding the marked position). Preferably, the localized second position(s) is/are marked in the second image(s). This marking can comprise displaying the localization information (position) in different manners, for example like an arrow, pointing to the dedicated position or like cross line or another geometrical shape, which is embedded in the image rendering process.

Referring now to the figures of the drawing in detail and first, particularly, to FIG. 1 thereof, there is shown a diagram of the basic principles of the navigation and localization system and method. As can be seen in FIG. 1 at least one image acquisition device, such as a mammography apparatus, is depicted in FIG. 1 on the left-hand side and identified with the reference symbol A (acquisition device). The invention generally is not limited to a specific mammography apparatus and it is also possible to use several different acquisition devices. Preferably, the system comprises one or more X-ray-based acquisition systems, such as an X-ray scanner or a computed tomograph (CT). The use of flat-panel X-ray detectors (FPXD) in mammography provides improved visualization and better efficiency within the medical process (improved throughput). A major advantage of this imaging technique is to be seen in that overlapping and overlaying tissues may be made visible by means of using a 3D imaging technique and specific algorithms. Unfortunately, the reading time and, therefore the cost of examination increases more than twofold with digital breast tomosynthesis images compared to full field digital mammography. An automatic navigation between different images and particularly, different DBT views, such as e.g. mediolateral oblique view (MLO view) and the cranio caudal view (CC view) and the corresponding views of FFDM images could significantly speed up the reading process. When a user clicks on a particular anatomical structure, e.g. a lesion, in one of the slices or two-dimensional images (in the following referred to as "first image"), the automatic navigation system according to this invention is able to point precisely the same or corresponding anatomical structure in the other views (refer to as "second image"). The navigation between different acquisitions or images (e.g. current image and prior images) or between two-dimensional FFDM images and three-dimensional DBT images is possible with the navigation and localization method and system according to present invention.

During image acquisition the breast B of a patient is typically compressed between two compression plates (or a compression plate and the detector cover surface), which in FIG. 1 show the reference numerals 10, 12. Digital tomosynthesis is, generally, similar to a computer tomography scan. During a CT scan, images are obtained from a full 360° rotation of a detector/X-ray source around a patient. In digital tomosynthesis (DBT), the rotation of the detector/source is limited to a specific rotation angle (e.g. 25°) as are the number of images that can be acquired. The three-dimensional reconstruction of this limited scan leads to very good in-plane resolution of the acquired images (e.g. 85 μm acquired and reconstructed pixel), but lower z-axis resolution (e.g. 1 mm thick slices). Still, this z-axis resolution provides enough separation of normal overlapping tissue to detect cancer or other structures that may otherwise go undetected.

The acquisition device A is coupled via a network NW to a computer-based processing station, which in FIG. 1 is identified with the reference symbol W. At the workstation W the acquired images are depicted on a (graphical) user interface.

Figure 2:
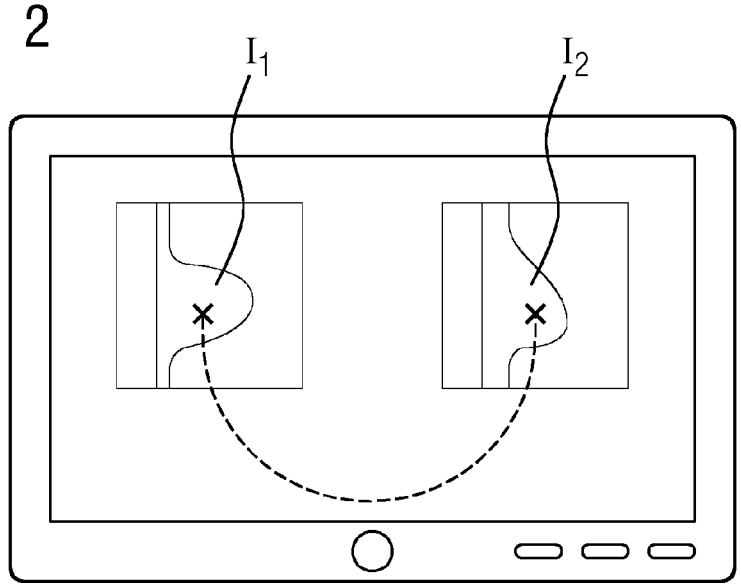
FIG. 2 illustrates a user interface with a first image from a breast in a first compression state and a second image of the breast in a second compression state where suspicious findings, marked on the first image are mapped to a corresponding position in the second image.

FIG. 2 shows the user interface in more detail. Typically, two different images I1, I2 are depicted in parallel. As can be seen in FIG. 2 a first image I1 from a breast in a first compression state is depicted on the left-hand side, whereas a second image I2 is depicted on the right-hand side, wherein the second image refers to the breast in a second compression state. As already described above, it is also possible to display different second images I2 which are to be viewed and visualized together with the first image. In order to provide as much medically relevant information as possible, typically, a DBT MLO view is compared with a DBT CC, FFDM MLO view and/or a FFDM CC view of the same patient breast.

After initializing and starting the process for navigating between and localizing dedicated positions the following steps are performed. If the user now clicks on a first position in the first image I1 (on the left-hand side), the system automatically will visualize and display a second position in the second image I2 which corresponds to the first position that has been originally marked by the user. The transfer of positions or the mapping is done fully automatically and is based on an automatic calculation, computation and processing of data on a (or more) computer(s). This transition or transformation of a first position in a second position of another image is depicted in FIG. 2 with a dotted, curved arrow form the first image I1 to the second image I2.

The position transformation algorithm according to present invention takes into account the displacement of the anatomical structures due to different breast positions (fixations) during acquisition. Even if the view position is exactly the same, for example a mediolateral oblique view in the first and second image I1, I2, it is practically impossible to position the breast in exactly the same way. There is always some amount of "rolling" or shifting of tissue present if the breast is repositioned. These factors are considered during position mapping according to the method of present invention.

As already mentioned above, in state of the art system it was known to use highly non-rigid registration methods for image comparison and mapping. These registration methods are typically based on internal breast structures and show the major drawbacks in processing time and resource requirements (as they are not suitable for real time implementation).

Therefore, present invention provides an alternative solution which allows avoiding the explicit registration of volumes and still provides for a precise navigation tool. The method and system for navigating between and localizing detected positions in different medical images according to an embodiment of present invention comprises the following steps:

a. A user marks a first position in a first image or slice in a 3D image.

b. An approximate position of the anatomical user-marked position in the second image I2 is roughly estimated. This rough estimation is based on mapping into a decompressed geometrical breast model. In this respect a thin-spline algorithm may be used. Alternatively, a more sophisticated model has been suggested in Wets, M. et al. "A Data-Driven Breast Decompression and Lesion Mapping from Digital Breast Tomosynthesis", proceedings of MICCAI 2012. This computer-based processing step could be executed online or on pre-computation decompressed breast model.

c. A computer aided detection algorithm is applied. Typically, the CAD algorithm is applied to both of the images, the first and the second image I1, I2. The algorithm is optimized for maximally high sensitivity. Preferably, the CAD algorithm is a computer-based machine learning algorithm, which could be trained by the output multiple classes of landmarks. The CAD algorithm could be applied in the local vicinity of the provided mark in the first image and of the roughly estimated position of the mapped mark in the second image.

d. As a final step, the rough estimation may be refined and improved in order to find a precise mapping of the (first) click point in the first image in a defined vicinity in the second image, which is a semantically closest (the most similar) anatomical structure in the second image I2.

e. Alternatively, in the absence of precisely mapped anatomical structure of the same class that is semantically close to the one provided by the user, other structures mapped in the vicinity of the clicked on structure are to provide the refined coordinate transformation that is then used to map the marked point in the image I1 to another point on image I2. For example, if the user clicked on an featureless background and not on a specific anatomical structure, then the other anatomical structures which the given CAD algorithm is able to detect will provide a refine coordinates transformation to map the marked position into the second image (e.g. by way of Random Sample Consensus method).

FIGS. 4 to 8 show different breast visualizations based on the method and system according to present invention. FIG. 4 shows an anatomical breast entity and the contours of the surface re-sampling planes in the MLO plane. A thin-plate spline-based (TPS) mapping may be used which maps each point of the input shape (first image I1) to its corresponding point in the target shape (second image I2). The TPS (thin-plate spline-based) mapping is computed based on two input shapes. The TPS mapping is a continuous mapping which interpolates between the known data points and can therefore be used for mapping a first position from within a first image (compressed breast) to a second position in the second image (predicted uncompressed breast).

FIG. 5 shows the first image I1 with the breast in a compressed state and showing a first position, which is depicted with a cross line in FIG. 5. This cross-lined position in I1 has to be transferred to a corresponding position in the second image I2 which, is depicted in FIGS. 6, 7 and 8. The second images I2 depict the breast B in a second (differently) compressed state. As can be seen in FIGS. 6 to 8 the corresponding second position is depicted with a geometrical shape (in FIG. 5 with a circle and in FIG. 6 with a square). FIG. 8 only shows a schematic visualization of the breast B in order to explain that also other second images I2 may be visualized with a corresponding second position, being marked in the respective second image I2. For example, the images, depicted in FIGS. 4 to 8, may refer to MR scans and/or DBT scans of a compressed and uncompressed breast, re-spectively.

With respect to the typical workflow of the method according to present invention with respect to a preferred embodiment is described.

After start of the procedure, in step 1 a first image I1 of the breast (typically in a first compressed state) is detected by way of an input interface.

In step 2 a second image I2 from the breast B is detected. Preferably, the acquisition of the second image I2 is also executed by means of the input interface. However, it is also possible to provide a second different input interface, in case the acquisition device is for the first and second images I1, I2 are not the same.

In step 3 a geometrical breast model is established or constructed. This breast model serves as input for the shape prediction algorithm. The shape prediction algorithm is based on a constructed statistical shape model of target shapes, i.e., of an uncompressed breast (as for example is depicted in FIGS. 5 to 8), from real patient data (e.g. extracted from MRI images of the same patient). According to a preferred embodiment of present invention the shape prediction algorithm is a machine learning-based shape prediction. In step 4 a shape prediction algorithm is applied in order to find a rough estimation for corresponding second position in the second image.

In step 5 a user input signal is received on a user interface. The user input signal represents a user-marking of the first position in the first image (for example in FIG. 5, I1).

Based on this user input, the method automatically processes this input for finding the second position. Therefore, in step 6, a CAD algorithm is applied for refining the rough estimation in the whole image or in the local vicinity/local vicinities of the first and second image positions, which has been extracted by applying the shape prediction algorithm in step 4. The CAD algorithm is trained to output image landmarks in the respective images I1, I2, such as lesions, clusters of calcifications and masses etc., as mentioned above.

In step 7 the second position in the second image I2 is detected, based on the refined rough estimation. As a major advantage of the present invention it should be mentioned that finding the second position is executed without explicit registration of the respective images I1, I2. The method is purely data driven and is based on a statistical shape model.

Figure 3:
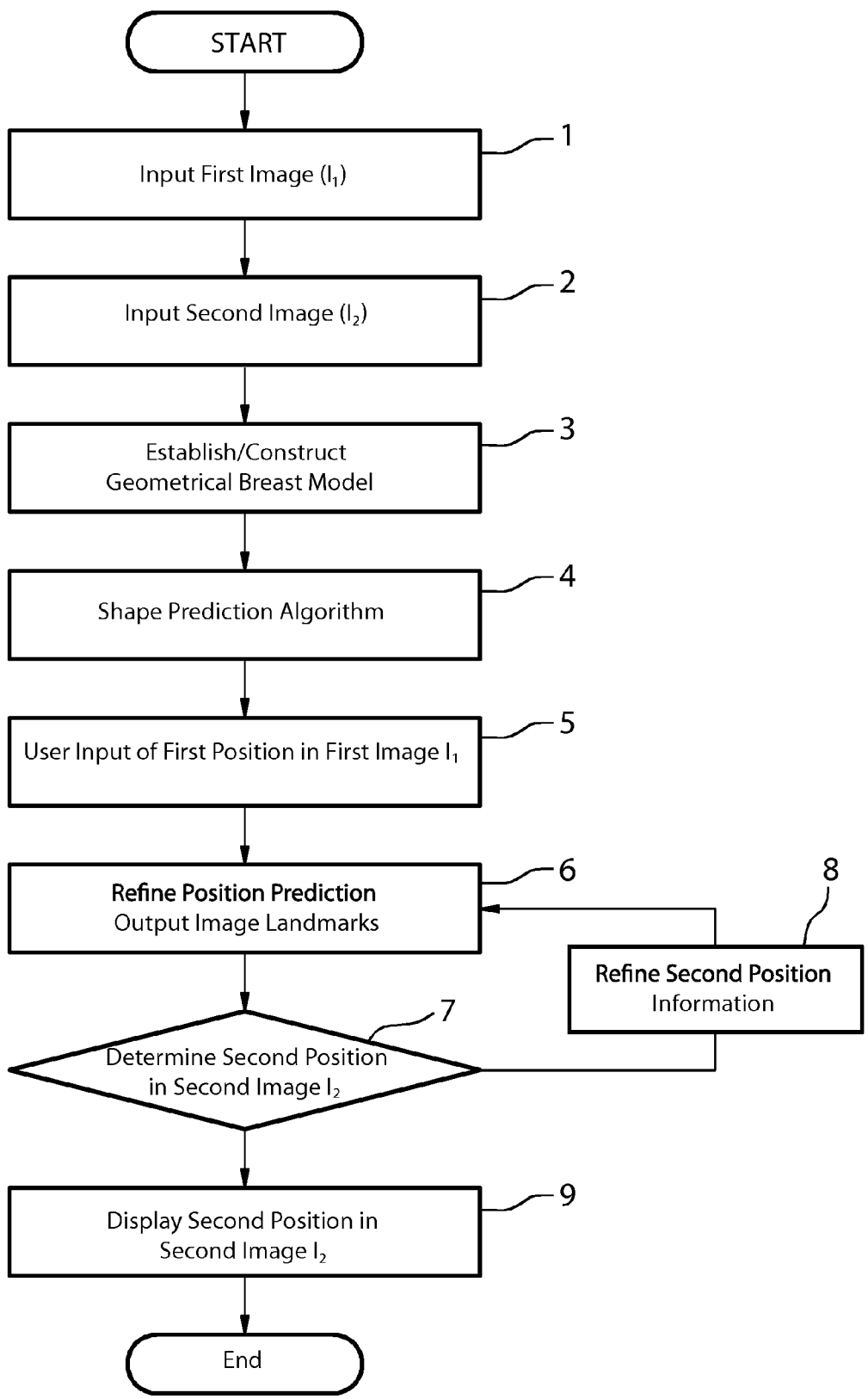
FIG. 3 illustrates a flowchart of the method according to an embodiment of the present invention.

In step 9 the detected second position (which has been localized in step 7) is displayed in the second image I2. As can be seen in FIG. 3 it is possible to execute the CAD algorithm and the localizing step iteratively or recursively in order to refine the second position, by cycling back through step 8.

In addition, in the foregoing detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the detailed description, with each claim standing on its own as defining separately claimed subject matter.

The above disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

The invention claimed is:

1. A method of navigating between and localizing dedicated positions in mutually different medical images, comprising:
    providing an input interface for acquiring a first image of a breast in a first compression state and a second image of the breast in a second compression state;
    receiving a user input signal on a user interface for marking a first position in the first image;
    applying a shape prediction algorithm to predict a decompressed shape for the first and second image and for obtaining a rough coordinate transformation mapping the first position provided by a user in the first image into a corresponding second position in the second image;
    applying a CAD algorithm to the first and second breast images to detect anatomical structures of multiple classes;
    refining the rough coordinate transformation for mapping locations in the first image into the corresponding second position in the second image by processing and matching landmarks of corresponding classes; and
    localizing the second position in the second image based on the refined coordinate transformation, and thereby executing the method steps without explicitly registering the first and second images.

2. The method according to claim 1, wherein the first and second images are digital breast tomosynthesis (DBT) images.

3. The method according to claim 1, wherein the shape prediction algorithm is based on a geometrical statistical breast model constructed based on a set of training data.

4. The method according to claim 3, wherein the statistical breast model is based on a set of shape parameters.

5. The method according to claim 1, which comprises performing the method steps on-line and/or in pre-computation.

6. The method according to claim 1, which comprises processing the shape prediction algorithm on-line and/or in pre-computation.

7. The method according to claim 1, wherein the CAD algorithm is a machine learning-based algorithm configured to process multiple classes of anatomical structures.

8. The method according to claim 1, which comprises performing the CAD algorithm step online in a local vicinity of a click point or a user-marked point and in local vicinity of a point mapped to another view or image scan in order to reduce a required computation time.

9. The method according to claim 1, which comprises, in the absence of a precisely mapped anatomical structure of the same class that is semantically close to the one provided by the user, using other structures mapped in a vicinity of a clicked-on structure to provide the refined coordinate transformation that is then used to map the marked point in the first image to another point on the second image by way of an automatic computation algorithm, comprising a Random Sample Consensus process.

10. A non-transitory computer program product loaded, or to be loaded, in a memory of a computer and having computer-executable instructions for executing the method according to claim 1 when the instructions are executed on the computer.

11. A computer-readable storage medium in non-transitory form with computer-executable instructions for executing the method according to claim 1.

12. A computerized system for navigating between mutually different medical images and for localizing dedicated positions in the images, the system comprising:
an input interface for inputting a first image acquired of an object in a first compression state and at least one second image of the object in a second compression state;
an input signal generation unit for receiving a user input signal from a user interface with a user-marked first position in the first image;
a shape prediction module configured to apply a shape prediction algorithm in order to predict the decompressed shape for the first image and the second image and to obtain a rough coordinate transformation mapping the user-marked first position in the first image into a corresponding second position in the at least one second image;
a CAD module configured for applying a CAD algorithm to the first and second images for detecting in the object anatomical structures of multiple classes;
a mapper configured to generate a refined coordinate transformation by refining the rough coordinate transformation mapping the locations in the first image into corresponding second positions in the at least one second image by processing and matching landmarks of corresponding classes; and
a localizer for localizing the second position in the at least one second image based on the refined coordinate transformation, said localizer executing the localizing process without explicitly registering the images, but only applying the refined coordinate transformation to the location in the first image.

13. The system according to claim 12, wherein the first and second images are digital breast tomosynthesis images and the object is a breast in mutually different compression states.

14. The system according to claim 13, wherein said shape prediction module is configured to execute a shape prediction algorithm based on a geometrical statistical breast model that is based purely on a set of training data.

15. The system according to claim 13, wherein the statistical breast model is based on a set of shape parameters.

16. The system according to claim 12, wherein said CAD module is implemented in common with said shape prediction module.

17. The system according to claim 12, wherein the images are acquired with an X-ray system having an X-ray emitting source, an X-ray detector and a computer node for image and data processing of the acquired images and the components are connected through a network.

18. The system according to claim 12, wherein the CAD algorithm is a machine learning-based algorithm which processes multiple classes of anatomical structures and the anatomical structures are anatomical landmarks selected from the group consisting of skin, nipple, pectoral muscle, and internal anatomical landmarks provided by the CAD algorithm.

19. The system according to claim 12, configured for executing a method for navigating between and localizing dedicated positions in mutually different medical images, the method comprising:
providing an input interface for acquiring a first image of a breast in a first compression state and a second image of the breast in a second compression state;
receiving a user input signal on a user interface for marking a first position in the first image;
applying a shape prediction algorithm to predict a decompressed shape for the first and second image and for obtaining a rough coordinate transformation mapping the first position provided by a user in the first image into a corresponding second position in the second image;
applying a CAD algorithm to the first and second breast images to detect anatomical structures of multiple classes;
refining the rough coordinate transformation for mapping locations in the first image into the corresponding second position in the second image by processing and matching landmarks of corresponding classes; and
localizing the second position in the second image based on the refined coordinate transformation, and thereby executing the method steps without explicitly registering the first and second images.

20. The system according to claim 12, comprising one or more processors for executing a computer program product which, upon being loaded into a working memory of said one or more processors is configured to execute a method for navigating between and localizing dedicated positions in mutually different medical images, the method comprising:
providing an input interface for acquiring a first image of a breast in a first compression state and a second image of the breast in a second compression state;
receiving a user input signal on a user interface for marking a first position in the first image;
applying a shape prediction algorithm to predict a decompressed shape for the first and second image and for obtaining a rough coordinate transformation mapping the first position provided by a user in the first image into a corresponding second position in the second image;
applying a CAD algorithm to the first and second breast images to detect anatomical structures of multiple classes;
refining the rough coordinate transformation for mapping locations in the first image into the corresponding second position in the second image by processing and matching landmarks of corresponding classes; and
localizing the second position in the second image based on the refined coordinate transformation, and thereby executing the method steps without explicitly registering the first and second images.

* * * * *